United States Patent [19]

Ida et al.

[11] Patent Number: 5,021,570

[45] Date of Patent: Jun. 4, 1991

[54] AQUEOUS SOLUTION CONTAINING FAT-SOLUBLE VITAMIN K

[75] Inventors: Katsumi Ida, Saitama; Takayuki Ikeuchi, Kounan; Masanori Kayano, Saitama, both of Japan

[73] Assignee: Eisai Co., Ltd., Tokyo, Japan

[21] Appl. No.: 376,708

[22] Filed: Jul. 7, 1989

[30] Foreign Application Priority Data

Jul. 11, 1988 [JP] Japan ................... 63-172463

[51] Int. Cl.$^5$ ................... A61K 31/12; A61K 47/00
[52] U.S. Cl. ................... 514/681; 514/777; 514/785; 514/786
[58] Field of Search ............. 514/681, 777, 785, 786

[56] References Cited

U.S. PATENT DOCUMENTS 4,840,970 6/1989 Ohasi et al. ................... 514/681

FOREIGN PATENT DOCUMENTS 59-055818 3/1984 Japan.
61-151132 7/1986 Japan.

Primary Examiner—Stanley J. Friedman
Assistant Examiner—Raymond J. Henley, II
Attorney, Agent, or Firm—Flynn, Thiel, Boutell & Tanis

[57] ABSTRACT

An aqueous solution containing fat-soluble vitamin K is prepared by adding vegetable oil(s), gycerol fatty acid ester(s) or sorbitan fatty acid ester(s) in an amount of 0.004 to 5% by weight, based on the whole aqueous solution, to an aqueous solution containing menatetrenone (vitamin $K_2$) or phytonadione (vitamin $K_1$) and hydrogenated lecithin.

6 Claims, No Drawings

AQUEOUS SOLUTION CONTAINING FAT-SOLUBLE VITAMIN K

This invention relates to an aqueous solution containing fat-soluble vitamin K, which solution contains specified stabilizer(s) and thus remains stable for a prolonged period of time.

DESCRIPTION OF THE PRIOR ART

Vitamin Ks are substances which have activity on blood coagulation and electron transport systems and they have been widely employed clinically. Recently it is desired to provide them in the form of an aqueous solution.

A known method for dissolving fat-soluble vitamins in water comprises using nonionic surfactants such as HCO-60 (mfd. by Nikko Chemical K.K.). However this process requires the use of a large amount of the surfactant HCO-60, which sometimes causes the liberation of histamine-like substances when the obtained preparation is to be used as an injection. Furthermore, such a preparation would sometimes cause disorders in the digestive tract and thus induce some undesirable side effects, such as diarrhea, when internally administered.

It is also known to use lecithin as an emulsifier. However the low emulsifying capability of lecithin makes it necessary to use a special device, namely, a pressure emulsifier. Further, the emulsion thus obtained shows a limited stability upon prolonged storage (cf. Japanese Patent Laid-Open No. 56315/1978).

Furthermore another known method for preparing a stable aqueous solution containing a fat-soluble vitamin comprises preliminarily dispersing and solubilizing the fat-soluble vitamin in an aqueous medium by using hydrogenated lecithin.

However the aqueous solution thus obtained shows an unsatisfactory stability upon prolonged storage. Thus there has been developed some processes for preparing an aqueous solution which remains stable for a prolonged period of time wherein hydrogenated lecithin is used together with an adjuvant (cf. Japanese Patent Laid-Open No. 104313/1984 and No. 25918/1985), though the effects thus achieved are yet unsatisfactory.

SUMMARY OF THE INVENTION

The present inventors have attempted to solve the abovementioned problems and to provide a stable aqueous solution containing vitamin $K_1$ or $K_2$, namely, active fat-soluble vitamin Ks. As a result, they have completed the present invention.

Accordingly, the present invention provides an aqueous solution containing fat-soluble vitamin K prepared by adding vegetable oil(s), glycerol fatty acid ester(s) or sorbitan fatty acid ester(s) in an amount of 0.004 to 5% by weight, based on the whole aqueous solution, to an aqueous solution containing menatetrenone (vitamin $K_2$) or phytonadione (vitamin $K_1$) and hydrogenated lecithin.

According to the present invention, this aqueous solution remains transparent or somewhat cloudy while showing little change upon prolonged storage. Namely, the present invention makes it possible to obtain an aqueous solution which is stable for a long time. More particularly, the aqueous solution containing fat-soluble vitamin K of the present invention is characterized by the property that it shows a high residual transmittance (%), which is calculated according to an equation as will be shown below based on the transmittances at 640 nm (T640) determined immediately after the preparation and after storing at 45° C. for 30 days, compared with those containing no stabilizer.

The term "residual transmittance (%)" used herein is calculated according to the following equation by utilizing the basic transmittance T640 of the composition immediately after the preparation and that determined, for example, after storing the composition at 45° C. for 30 days:

residual transmittance (%)=(T640 after storing)/(basic T640)×100

In the present invention, stabilizer(s) are added to an aqueous solution containing vitamin $K_1$ or $K_2$ and hydrogenated lecithin at the following ratio.

From the clinical point of view, an aqueous solution of an active vitamin K should have a concentration of 0.1 to 1.0% by weight, usually 0.2 to 0.5% by weight. When the aqueous solution is to be used as an injection, in particular, concentrations around 0.5% by weight are often employed. When the aqueous solution is to be used as a syrup, on the other hand, concentrations around 0.2% by weight are often employed. However the amount of the active vitamin Ks is not restricted thereby.

Preferable examples of the hydrogenated lecithin to be used in the present invention are hydrogenated soybean and yolk lecithins. This hydrogenated lecithin preferably comprises at least 85% of phospholipids and at least 60%, based on the phospholipids, of phosphatidylcholine and has an iodine number of 10 to 60, still preferably 25 to 50 (cf. Japanese Patent Laid-Open No. 62010/1980). The aqueous solution of the present invention preferably contains 0.05 to 3% by weight of the hydrogenated lecithin.

Examples of the vegetable oils to be used in the present invention include soybean, sesame, olive, cotton seed, tsubaki, rapeseed, peanut and corn oils.

Examples of the glycerol fatty acid esters to be used in the present invention include triesters of glycerol and fatty acids having 8 to 12 carbon atoms and mono- and triesters of glycerol and oleic, stearic or palmitic acid.

Examples of the sorbitan fatty acid esters to be used in the present invention include mono-, sesqui- and triesters of sorbitan and oleic, stearic or palmitic acid.

In the present invention, the amount of the stabilizer(s) selected from among said vegetable oils, glycerol fatty acid esters and sorbitan fatty acid esters may vary depending on the purpose of application of the aqueous solution to be prepared. The stabilizer(s) may be used in an amount of 0.004 to 5% by weight, preferably 0.02 to 1.5% by weight, based on the whole aqueous solution. In practice, 0.01 to 3 parts by weight of the stabilizer(s) may be added per part by weight of the vitamin $K_1$ or $K_2$ though the present invention is not specifically restricted thereby.

When the amount of the stabilizer(s) is less than 0.004% by weight of the whole aqueous solution, no stabilization of the aqueous solution can be achieved. When it exceeds 5% by weight, on the other hand, the aqueous solution would become undesirably cloudy at the mixing stage.

The aqueous solution of the present invention may be appropriately prepared. An example of the preparation thereof is as follows.

First, purified hydrogenated yolk lecithin or purified hydrogenated soybean lecithin and a stabilizer selected from among vegetable oils, glycerol fatty acid esters and sorbitan fatty acid esters are added to vitamin $K_1$ or $K_2$ together with a small amount of water. The resulting mixture is preferably heated to 70° to 95° C. and homogeneously dispersed under ultrasonic vibration or stirring.

To the crude dispersion thus obtained were added other components and water. By homogeneously dispersing, the aqueous solution of the present invention can be obtained.

When the aqueous solution of the present invention is to be used as an injection, it may be filtered, filled in an ampule and sterilized.

The abovementioned other components may be selected from among, for example, buffers such as neutral amino acids including glycine, bactericides and tonicity agents, without restriction. However it is preferable to avoid the addition of any electrolyte components, since they would inhibit the dispersion, in particular, solubilization.

Furthermore, some portion of the water in the aqueous solution of the present invention may be replaced with water-soluble solvent(s) such as ethanol, propylene glycol, D-sorbitol, low molecular weight polyethylene glycol or glycerol. These solvents are highly effective for remarkably shortening the time required for the rough dispersion of the vitamin $K_1$ or $K_2$ during the preparation of the aqueous solution. Namely, the vitamin $K_1$ or $K_2$ may be preliminarily dispersed in a water-soluble solvent by using the hydrogenated lecithin and then water is added thereto. Thus the time required for the solubilization can be shortened, compared with the abovementioned case wherein the vitamin $K_1$ or $K_2$ and hydrogenated lecithin are directly mixed together and then water is added thereto.

When the water-soluble solvent(s) are to be added in order to facilitate the preparation of the aqueous solution, they may be preferably added in an amount of 1 to 50 parts by weight per part by weight of the vitamin $K_1$ or $K_2$. It is further preferable that 2 to 10% by weight of said solvent(s) are contained in the aqueous solution of the present invention.

When the aqueous solution of the present invention is to be used as an injection, tonicity agents commonly employed in the art, for example, sugars and/or sugar alcohols such as glucose, xylitol, sorbitol or mannitol may be added thereto. Namely, the addition of these tonicity agents would never deteriorate the effects of the present invention. The use of these additives is rather effective in order to inhibit the formation of cloudiness in the sterilization of the injection product. These tonicity agents may be preferably used in an amount of 1 to 10% by weight based on

EXAMPLE

To further illustrate the present invention, and not by way of limitation, the following Examples will be given.

EXAMPLE 1

0.4 part by weight of menatetrenone, 0.8 part by weight of purified hydrogenated yolk lecithin, 0.2 part by weight of "olive oil," 4 parts by weight of glycerol and 6 parts by weight of distilled water were exposed to ultrasonic vibration in an ultrasonic emulsifying device for 10 minutes while cooling in water. Then 10 parts by weight of sorbitol and distilled water were added thereto to thereby give a total amount of 200 parts by weight. After continuing the ultrasonic vibration for 30 minutes, 1 part by weight of glycine was added and the pH value of the mixture was adjusted to 7.2 with sodium hydroxide. The mixture was filtered through a membrane filter and filled in a brown 5-ml ampule. After purging with nitrogen, heat-sealing and free-flowing steam sterilization, an injection was obtained.

EXAMPLE 2

0.4 part by weight of menatetrenone, 0.56 part by weight of purified hydrogenated soybean lecithin, 0.1 part by weight of cotton seed oil, 4 parts by weight of propylene glycol and 8 parts by weight of distilled water were exposed to ultrasonic vibration in an ultrasonic emulsifying device for 10 minutes while cooling in water. The 10 parts by weight of mannitol and distilled water were added thereto to thereby give a total amount of 200 parts by weight. After continuing the ultrasonic vibration for 30 minutes, 1 part by weight of alanine was added and the pH value of the mixture was adjusted to 7.2 with sodium hydroxide. The mixture was filtered through a membrane filter and filled in a brown 5-ml ampule. After purging with nitrogen, heat-sealing and free-flowing steam sterilization, an injection was obtained.

EXAMPLE 3

0.4 part by weight of menatetrenone, 0.8 part by weight of purified hydrogenated yolk lecithin, 0.2 part by weight of sorbitan monostearate, 4 parts by weight of glycerol and 5 parts by weight of distilled water were exposed to ultrasonic vibration in an ultrasonic emulsifying device for 10 minutes while cooling in water. Then distilled water was added thereto to thereby give a total amount of 60 parts by weight and the ultrasonic vibration was continued for 30 minutes. Separately, 120 parts by weight of sorbitol, 0.14 part by weight of sodium benzoate and distilled water were mixed to thereby give a total amount of 140 parts by weight. These materials were mixed together to thereby give an internal syrup.

EXAMPLE 4

Five parts by weight of menatetrenone, 8 parts by weight of purified hydrogenated soybean lecithin, 2 parts by weight of sesame oil, 50 parts by weight of glycerol and 80 parts by weight of distilled water were stirred in a homomixer for 10 minutes while cooling in water. Then 50 parts by weight of sorbitol and distilled water were added thereto to thereby give a total amount of 1000 parts by weight. After stirring in the homomixer for 30 minutes, 5 parts by weight of glycine was added and the pH value of the mixture was adjusted to 7.2 with sodium hydroxide. The mixture was filtered through a membrane filter and filled in a brown 5-ml ampule. After purging with nitrogen, heat-sealing and free-flowing steam sterilization, an injection was obtained.

EXAMPLE 5

0.5 part by weight of menatetrenone, 0.8 parts by weight of purified hydrogenated soybean lecithin, 0.2 part by weight of glycerol tristearate, 5 parts by weight of glycerol and 7 parts by weight of distilled water were exposed to ultrasonic vibration in an ultrasonic emulsifying device for 10 minutes while cooling in water. Then 5 parts by weight of sorbitol and distilled water were added thereto to thereby give a total amount of 100 parts by weight. After continuing the ultrasonic vibration for 30 minutes, 0.3 part by weight of taurine was added and the pH value of the mixture was adjusted to 7.2 with sodium hydroxide. The mixture was filtered through a membrane filter and filled in a brown 2-ml ampule. After purging with nitrogen, heat-sealing and free-flowing steam sterilization, an injection was obtained.

EXAMPLE 6

0.5 part by weight of phytonadione, 0.8 part by weight of purified hydrogenated soybean lecithin, 0.2 part by weight of sesame oil, 5 parts by weight of glycerol and 7 parts by weight of distilled water were exposed to ultrasonic vibration in an ultrasonic emulsifying device for 10 minutes while cooling in water. Then 5 parts by weight of sorbitol and distilled water were added thereto to thereby give a total amount of 100 parts by weight. After continuing the ultrasonic vibration for 30 minutes, 0.3 part by weight of taurine was added and the pH value of the mixture was adjusted to 7.2 with sodium hydroxide. The mixture was filtered through a membrane filter and filled in a brown 2-ml ampule. After purging with nitrogen, heat-sealing and free-flowing steam sterilization, an injection was obtained.

Effects of the Invention

The effects of the invention will be illustrated by the following Test Examples.

TEST EXAMPLE 1

0.5 part by weight of menatetrenone, 0.8 part by weight of each hydrogenated lecithin shown in Table 1, 5 parts by weight of glycerol, 8 parts by weight of distilled water and each stabilizer shown in Table 1 in the specified amount were subjected to ultrasonic vibration in an ultrasonic vibrator (TOMY SEIKO UR-200P) for 10 minutes while cooling in water. Then 5 parts by weight of sorbitol and distilled water were added thereto to thereby give a total amount of 100 parts by weight. After continuing the ultrasonic vibration for 30 minutes, 0.5 part by weight of taurine was added and the pH value of the mixture was adjusted to 7.2. The mixture was filtered through a membrane filter and filled in a brown 2-ml ampule. After purging with nitrogen, heat-sealing and free-flowing steam sterilization, the transmittance at 640 nm (T640nm %) was determined. Then each sample was stored at 45° C. for one month and the transmittance (T640nm %) was determined again. Thus the residual transmittance was calculated.

Table 1 shows the results.

TABLE 1

| | | Stabilizer (% by wt.) | | Initial $640_{nm}\%$ (A) | After 1 m. at 45° C. $T_{640nm}\%$ (B) | Residual transmittance B/A × 100% |
|---|---|---|---|---|---|---|
| Menatetrenone (0.5% by wt.) | Purified hydrogenated soybean lecithin (0.8% by wt.) | none | | 66.8 | 48.4 | 72.5 |
| | | Sesame oil | 0.2 | 75.0 | 74.5 | 99.3 |
| | | | 1.0 | 34.2 | 34.6 | 101.2 |
| | | Soybean oil | 0.2 | 70.3 | 69.4 | 98.7 |
| | | | 1.0 | 20.6 | 21.2 | 102.9 |
| | | Myglyol 812*[1] | 0.2 | 68.4 | 62.9 | 92.0 |
| | | | 1.0 | 31.8 | 29.3 | 92.1 |
| | | Glycerol monooleate | 0.2 | 65.2 | 51.4 | 78.8 |
| | | | 1.0 | 5.6 | 4.5 | 80.4 |
| | | Glycerol monostearate | 0.2 | 62.0 | 57.3 | 86.3 |
| | | | 1.0 | 14.0 | 12.0 | 85.7 |
| | | Sorbitan monooleate | 0.2 | 72.1 | 61.5 | 85.3 |
| | | | 1.0 | 36.2 | 31.3 | 85.8 |
| | | Sorbitan sesquioleate | 0.2 | 57.8 | 45.7 | 79.1 |
| | | | 1.0 | 8.5 | 7.8 | 91.8 |
| | | Sorbitan trioleate | 0.2 | 68.4 | 61.8 | 90.4 |
| | | | 1.0 | 6.2 | 5.4 | 87.1 |

| | | Stabilizer (% by wt.) | | Initial $T_{640nm}\%$ (A) | After 1 m. at 45° C. $T_{640nm}\%$ (B) | Residual transmittance B/A × 100% |
|---|---|---|---|---|---|---|
| Menatetrenone (0.5% by wt.) | Purified hydrogenated yolk lecithin (0.8% by wt.) | none | | 24.2 | 13.2 | 54.5 |
| | | Sesame oil | 0.2 | 30.1 | 31.0 | 103.0 |
| | | | 1.0 | 4.6 | 5.0 | 108.7 |
| | | Soybean oil | 0.2 | 34.2 | 34.6 | 101.2 |
| | | | 1.0 | 4.0 | 4.3 | 107.5 |
| | | Myglyol 812 | 0.2 | 25.1 | 19.3 | 76.9 |
| | | | 1.0 | 15.7 | 13.0 | 82.8 |

Note
*[1] A mixture of glycerol esters of fatty acids having 8 to 12 carbon atoms.

As is apparent from Table 1, the samples comprising vitamin $K_2$ and hydrogenated lecithin together with vegetable oils such as sesame oil, soybean oil or Myglyol 812, glycerol monooleate, glycerol monostearate, sorbitan monooleate, sorbitan sesquioleate or sorbitan trioleate showed each a high residual transmittance after storage at 45° C. for one month.

TEST EXAMPLE 2

0.5 part by weight of menatetrenone, 0.8 part by weight of purified hydrogenated soybean lecithin, 5 parts by weight of glycerol, 8 parts by weight of distilled water and 0.02 to 5.0 parts by weight of sesame oil were treated in the same manner as the one described in Test Example 1. Thus the effect of the concentration of sesame oil as a stabilizer was examined.

Table 2 shows the results.

TABLE 2

| | Stabilizer (% by wt.) | | Initial $T_{640nm}\%$ (A) | After 1 m. at 45° C. $T_{640nm}\%$ (B) | Residual transmittance (B)/(A) × 100 |
|---|---|---|---|---|---|
| Menatetrenone (0.5% by wt.) | Purified hydrogenated soybean lecithin (0.8% by wt.) | none | 66.8 | 48.4 | 72.5 |
| | | Sesame oil 0.02 | 68.0 | 55.1 | 81.0 |
| | | 0.04 | 71.9 | 62.9 | 87.5 |
| | | 0.06 | 72.0 | 65.9 | 91.5 |
| | | 0.08 | 76.4 | 71.9 | 94.1 |
| | | 0.1 | 78.5 | 75.5 | 96.2 |
| | | 0.2 | 75.0 | 74.5 | 99.3 |
| | | 0.5 | 50.5 | 50.1 | 99.2 |
| | | 1.0 | 34.2 | 34.6 | 101.2 |
| | | 1.5 | 12.5 | 12.0 | 96.0 |
| | | 5.0 | 0.1 | 0.1 | — |

As is apparent from Table 2, the samples comprising 0.02 to 1.5% by weight of sesame oil as a stabilizer showed each a high residual transmittance after storage at 45° C. for one month.

We claim:

1. An aqueous solution comprising (A) about 0.5 wt. %, based on the weight of said aqueous solution, of fat-soluble vitamin K selected from the group consisting of vitamin $K_1$ and vitamin $K_2$, (B) about 0.8 wt. %, based on the weight of said aqueous solution, of hydrogenated lecithin, (C) from 0.02 to 1.0 wt. %, based on the weight of said aqueous solution, of stabilizer selected from the group consisting of (i) a triester of glycerol with fatty acids having 8 to 12 carbon atoms, and (ii) a monoester and triester of glycerol with oleic acid, stearic acid or palmitic acid, and (D) water, said stabilizer being effective to maintain the transmittance of said aqueous solution at 640 nm, when measured after storing said aqueous solution at 45° C. for 30 days, at a value of at least 76.9% of said transmittance of said aqueous solution prior to said storing of same.

2. The aqueous solution as claimed in claim 1 in which said stabilizer is selected from the group consisting of a mixture of glycerol esters of fatty acids having 8 to 12 carbon atoms, glycerol monooleate, glycerol monostearate and glycerol tristearate.

3. An aqueous solution comprising (A) about 0.5 wt. %, based on the weight of said aqueous solution, of fat-soluble vitamin K selected from the group consisting of vitamin $K_1$ and vitamin $K_2$, (B) about 0.8 wt. %, based on the weight of said aqueous solution, of hydrogenated lecithin, (C) from 0.02 to 1.0 wt. %, based on the weight of said aqueous solution, of stabilizer selected from the group consisting of a monoester, a sesquiester and a triester of sorbitan with oleic acid, stearic acid or palmitic acid, and (D) water, said stabilizer being effective to maintain the transmittance of said aqueous solution at 640 nm, when measured after storing said aqueous solution at 45° C. for 30 days, at a value of at least 79.1% of said transmittance of said aqueous solution prior to said storing of same.

4. The aqueous solution as claimed in claim 3 in which said stabilizer is selected from the group consisting of sorbitan monooleate, sorbitan sesquioleate, sorbitan trioleate and sorbitan monostearate.

5. An aqueous solution comprising (A) about 0.5 wt. %, based on the weight of said aqueous solution, of fat-soluble vitamin K selected from the group consisting of vitamin $K_1$ and vitamin $K_2$, (B) about 0.8 wt. %, based on the weight of said aqueous solution, of hydrogenated lecithin, (C) from 0.02 to 1.5 wt. %, based on the weight of said aqueous solution, of vegetable oil as a stabilizer, and (D) water, said stabilizer being effective to maintain the transmittance of said aqueous solution at 640 nm, when measured after storing said aqueous solution at 45° C. for 30 days, at a value of at least 81.0% of said transmittance of said aqueous solution prior to said storing of same.

6. An aqueous solution as claimed in claim 5 in which said stabilizer is selected from the group consisting of soybean oil, sesame oil, olive oil, cottonseed oil, tsubaki oil, rapeseed oil, peanut oil and corn oil.

* * * * *